United States Patent [19]

Sarneel

[11] Patent Number: Plant 5,395

[45] Date of Patent: Jan. 22, 1985

[54] CARNATION NAMED CAPPELLO

[75] Inventor: J. F. Sarneel, Nieuwveen, Netherlands

[73] Assignee: M. Lek en Zonen, B.V., Nieuwveen, Netherlands

[21] Appl. No.: 508,865

[22] Filed: Jun. 29, 1983

[51] Int. Cl.[3] ..... A01H 5/00

[52] U.S. Cl. ..... Plt./72

[58] Field of Search ..... Plt./72

*Primary Examiner*—Robert E. Bagwill

*Attorney, Agent, or Firm*—Chas. W. Rummler; John B. Lungmus

[57] ABSTRACT

A new carnation cultivar distinguished by its continuous and profuse production of very pleasing, bright pink blossoms of medium size, borne raceme with more than three per stem on medium strong peduncles of medium length, the plant being a tall, spray type with a vigorous, rapid and sturdy growth habit and an average height of about one meter.

2 Drawing Figures

BACKGROUND OF THE NEW PLANT

This carnation variety originated as a seedling of unknown parentage growing among hybrid plants produced by cross-pollinating selected seedlings of unknown origin, maintained in my greenhouse at Nieuwveen, Netherlands for breeding purposes, with the object of developing plants having improved quality and flower production. This plant was selected by me for asexual propagation and character evaluation because of its high production of blossoms having an attractive dark pink color and propagation of this new plant, by cuttings, through successive generations at Nieuwveen, Netherlands has shown that its novel characteristics hold true from generation to generation and appear to be firmly fixed.

This new plant is now being propagated on a commercial scale, by cuttings, at Nieuwveen, Netherlands and at Wheat Ridge, Colo.

DESCRIPTION OF THE DRAWINGS

My new variety of carnation plant is illustrated by the accompanying photographic drawings which show, in full color, in the right hand view, a group of stems bearing buds, partially opened flowers and full blooms; and in the left hand view, a face view of a fully opened flower; the colors shown being as nearly true as it is reasonably possible to obtain by conventional photographic procedures.

DESCRIPTION OF THE NEW PLANT

The following is a detailed description of my new carnation variety based upon observations of greenhouse grown plants made at Wheat Ridge, Colo. in March and April 1983, the color designations being according to The R.H.S. Colour Chart of The Royal Horticultural Society at London, England.

THE PLANT

Origin: Seedling.
Parentage: Unknown.
Classification:
*Botanic.*—*Dianthus caryophyllus.*
*Commercial.*—Greenhouse carnation for cut flowers.
Form: Bush, with tall spray shape.
Height: About one meter.

Growth: Upright, vigorous and very rapid, with alternate branching, and with a strong and medium sturdy habit.
Foliage: Abundant in quantity.
*Character of leaf.*—About 10 cm. long, sessile and having irregularly crenated margins.
*Texture.*—Leathery.
*Color.*—Upper side — Blue Green. Under side — Blue Green.

THE BUD

Size: Medium.
*Diameter.*—About 15 mm.
*Length.*—About 30 mm.
Shape: Pear shaped, becoming generally cylindrical just before opening to show petal color.
Rate of opening: Rapid; with mature bud, the flowers appear five days after sepals begin to divide.
Color:
*When sepals first divide.*—Pink.
*When petals begin to unfurl.*—Pink.
Sepals: At the beginning, the sepals are hooded over the bud and when the flowers open, the sepals stand up. The sepals have a pointed tip and angle outwardly about 60°.
Calyx:
*Shape.*—Cylindrical.
*Size.*—Medium long.
*Splitting.*—The calyx does not split.
*Aspect.*—Smooth.
Flower stem:
*Character.*—Strong and erect.
*Color.*—Blue Green.

THE FLOWER

Blooming habit: Continuous and profuse production of flowers.
Flower size: Medium.
*Diameter.*—About 55 mm.
*Depth.*—About 30 mm.
Borne: Singly in raceme with more than three per stem.
Shape:
*When blooms first open.*—Flattened convex.
*When bloom matures.*—Considerably more convex.
Petalage:
*Number of petals.*—Thirty-one.
*Arrangement.*—Imbricated.

*Form.*—Fan shaped with transversely undulating surface, crenated margin and rounded apex.

*Texture.*—Soft.

*Appearance.*—Velvety.

*Color.*—Both upper and reverse side of petals — R.H.S. 52B-C with a somewhat lighter pink color at the base.

Claw:

*Length.*—About 25 mm.

*Color.*—Pale Green.

Discoloration after full bloom: The bloom may lighten in color as flower ages.

Effect of weather: The bloom is not affected by either wet or hot weather.

Persistence: The flower will hang on and dry.

Fragrance: Weak.

Lasting quality: As cut flower — 10 to 20 days.

REPRODUCTIVE ORGANS

Stamens:

*Anthers.*—Many in number arranged evenly. Size: About 3 to 4 mm. Color — Straw-Yellow.

*Filaments.*—Length — About 23 mm. Color — Almost White.

*Pollen.*—Color — Pale Pink.

Pistils: Two, sometimes fascieted.

*Styles.*—Length — 15 mm. Color — White at bottom, Pink on top.

*Stigmas.*—Color — Pale Pink.

Characteristics of ovaries: Spindle shaped and Light Green in color.

I claim:

1. The new and distinct carnation cultivar, substantially as herein shown and described, characterized by its profuse year round production of medium sized, bright pink blossoms.

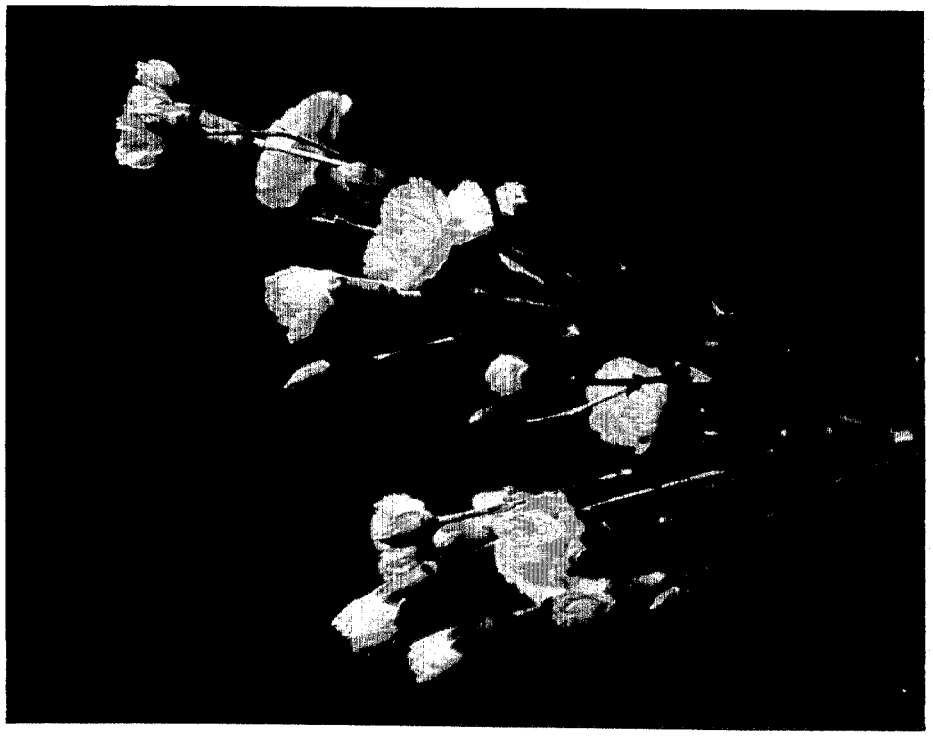
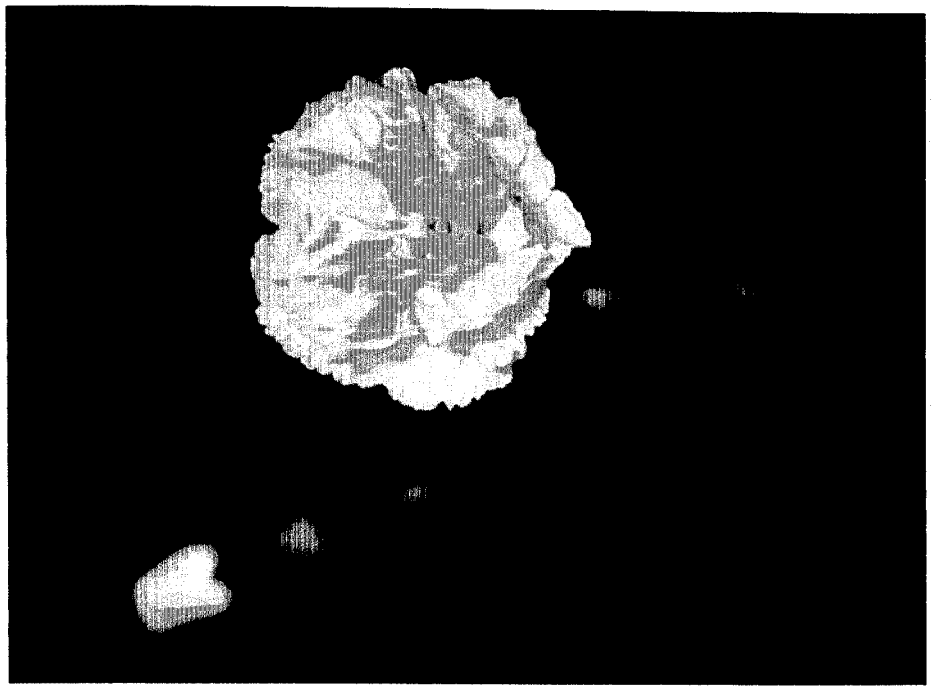

* * * * *